United States Patent [19]

Schanz

[11] Patent Number: 4,639,362

[45] Date of Patent: Jan. 27, 1987

[54] PROCESS FOR THE PRODUCTION OF MAGALDRATE

[75] Inventor: Klaus Schanz, Dannstadt-Schauernheim, Fed. Rep. of Germany

[73] Assignee: Giulini Chemie GmbH, Ludwigshafen am Rhein, Fed. Rep. of Germany

[21] Appl. No.: 708,553

[22] Filed: Mar. 5, 1985

[30] Foreign Application Priority Data

Mar. 8, 1984 [DE] Fed. Rep. of Germany ....... 3408463

[51] Int. Cl.$^4$ .......................... C01F 1/00; A61K 33/08; A61K 33/04
[52] U.S. Cl. .................................... 423/554; 423/556; 423/600; 423/629; 424/157
[58] Field of Search ............... 423/117, 554, 556, 600, 423/629; 424/157

[56] References Cited

U.S. PATENT DOCUMENTS

| 3,857,938 | 12/1974 | Rovati et al. | 424/156 |
| 4,105,579 | 8/1978 | Glasscock | 424/156 X |
| 4,443,433 | 4/1984 | Knecht et al. | 424/157 |
| 4,482,542 | 11/1984 | Schneider et al. | 424/157 |
| 4,539,195 | 9/1985 | Schanz et al. | 423/419 P |

FOREIGN PATENT DOCUMENTS

| B 36762 | 11/1956 | Fed. Rep. of Germany. | |
| 49-38997 | 10/1974 | Japan | 424/157 |

*Primary Examiner*—Brian E. Hearn
*Assistant Examiner*—O. Chaudhuri
*Attorney, Agent, or Firm*—Spencer & Frank

[57] ABSTRACT

Novel process for the production of magaldrate by the reaction of active aluminum hydroxide with a water soluble, sulfate containing compound and active magnesium oxide and/or magnesium hydroxide in stoichiometric quantities in the presence of water.

5 Claims, 2 Drawing Figures

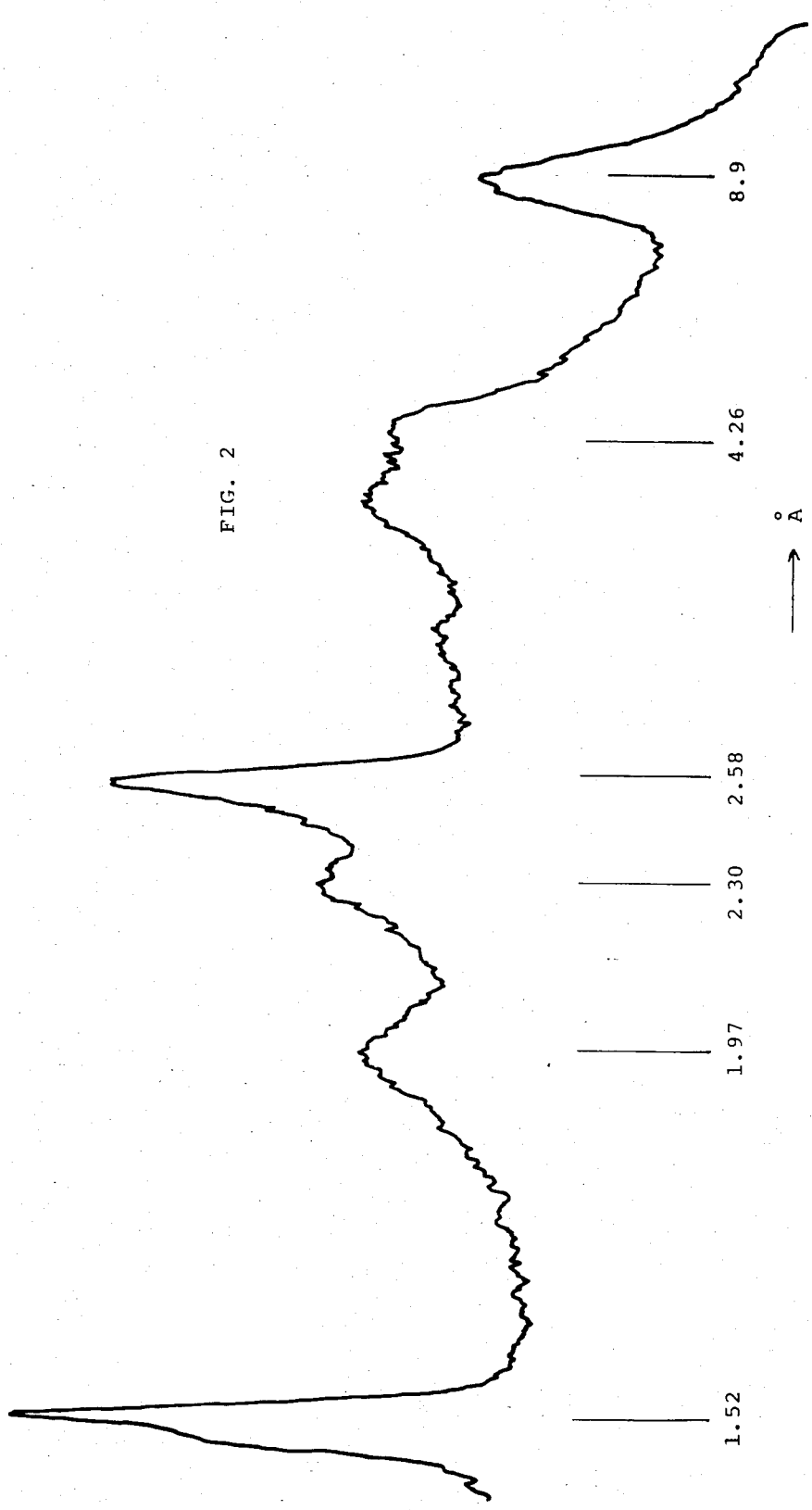

PROCESS FOR THE PRODUCTION OF MAGALDRATE

BACKGROUND OF THE INVENTION

The present invention relates to a novel process for the production of magaldrate and to the use of the product produced thereby in pharmaceutical products, particularly antacids.

According to United States Pharmacopoeia XXI/1985, First Supplement, USP-NF page 1740, magaldrate is an aluminum magnesium hydroxide sulfate of the formula $$Al_5Mg_{10}(OH)_{31}(SO_4)_2 \cdot xH_2O$$

where x is preferably 0–6,77 (according to United States Pharmacopoeia XXI/1985, but can be also greater than 6,77.

It may be manufactured and used in hydrated as well as dehydrated form and is considered a chemical combination of aluminum hydroxide and magnesium hydroxide. Moreover, it contains not less than 29.0% and not more than 40.0% of the equivalent quantity of MgO and not less than 18% and not more than 26% of the equivalent quantity of $Al_2O_3$. With reference to magaldrate that is free of water, the formula yields a theoretical sulfate content of about 17.5%.

The USP standard magaldrate is characterized by having a maximum water soluble sulfate content of 1.9%, and a specific X-ray diffraction spectrum in the range of 0.18 to 2.20 nm, among other features.

Magaldrate is used as the active antacid ingredient in known antacids. The advantageous characteristics of these magaldrate containing antacids, such as fast and long lasting acid neutralization, long-term stability, distinct adsorption capability with respect to pepsin, bile acid and lysolecithin are the result of the composition and structure of magaldrate.

Magaldrate, formerly called magnesium aluminate hydrate, has been produced for a long time. In the method for producing magaldrate according to German Patent Application No. B 36,762 IVa/30 h, a magnesium salt solution is added under intensive mixing to a highly basic alkalialuminate solution containing three to five moles of $Na_2O$ or another alkali oxide for each mole of $Al_2O_3$ at a temperature which does not exceed 50° C. and in such quantities that the ratio of aluminum to magnesium is 1:0.9 to 3. The resulting precipitate is separated from the solution, washed and possibly gently dried. The ratio of aluminum to magnesium employed is perferably 1:2.

Although in the examples of the above-described reference magnesium sulfate is used exclusively, the process is not limited to this magnesium salt. Obviously, for this reason magaldrate was not formulated as a sulfate containing compound in the German patent application or in earlier U.S. Pharmacopoeae.

Using the process of German Patent Application No. B 36,762 IVa/30h at an atomic ratio of Mg:Al of 2:1, only after thoroughly washing the filter cake is magaldrate of the stated formula obtained. After washing with water, the filter cake can be homogenized into a paste and can be processed, with the addition of preservatives, flavoring agents and other adjuvants, to produce a liquid antacid preparation. Alternatively, the washed filter residue or the paste can be dried and used as the active antacid ingredient in the manufacture of antacid tablets or powders.

Surprisingly, it has now been discovered that the prior art method can be replaced by a novel, significantly better method. Precipitation, filtration and, particularly, washing are known to be time consuming and are, therefore, operations which reduce production capacity in the prior art process, and considerably increase the manufacturing costs compared to processes for the manufacture of other active antacid substances, such as aluminum hydroxide gel and aluminum phosphate gel. For example, a washing time of about 200 minutes is required to wash aluminum hydroxide gel produced according to the process of German Patent No. 1,921,999 in a 100 m² filter press. However, magaldrate produced according to the above-cited German patent application requires about four times the amount of time, i.e. approximately 800 minutes.

A further drawback of this prior art process is that filter cake concentrations of only about 10 to 13 weight percent magaldrate can be obtained with present-day filtration techniques employing rotary filters or filter presses. Consequently, in the subsequent formulation, only those end products whose magaldrate concentration lies slightly below this concentration range can be obtained. Accordingly, the liquid antacids containing magaldrate that are presently commercially available comprise only 9 weight percent magaldrate, on the average.

SUMMARY OF THE INVENTION

It is the object of the present invention to provide a novel process for the manufacture of magaldrate which, when compared with the prior art process, provides both labor saving and economic advantages by eliminating precipitation, washing and homogenization, and makes possible new pharmaceutical applications by providing a more concentrated product.

According to the present invention, active aluminum hydroxide is reacted, in the presence of water, with at least one water soluble sulfate containing compound and with active magnesium oxide and/or magnesium hydroxide in stoichiometric quantities to produce a magaldrate paste, which is then dried if required. The resulting magaldrate paste contains no ancillary products (impurities), and filtration, washing and rehomogenization processes are not required. The reaction product can be processed directly into liquid antacids containing magaldrate or, alternatively, can be converted to magaldrate power by drying, preferably by spray drying. Moreover, it has been found that, depending on the consistency of the starting materials, the concentrations and viscosities of the resulting magaldrate pastes can be varied over a broad range, which is of particular advantage for pharmaceutical use. This is a surprising result which cannot be derived from the prior art. It is now possible, according to this invention, to produce pastes which contain up to 30 weight percent magaldrate.

At this point, it should be pointed out that carbonate-free magaldrates are obtained only if the pH is less than 7 during the reaction of active aluminum hydroxide with the compound containing the sulfate ion. If the pH equals 7 or is greater than 7, the products contain carbon dioxide.

Active aluminum hydroxide is known. It may be produced according to various processes and is an amorphous, finely divided, particulate aluminum hydroxide gel which dissolves quickly in dilute acid. For example, during the precipitation from aluminum salt solutions using bases, alkali carbonates in particular are produced. The aluminum hydroxide gel produced according to German Patent No. 1,921,999, which contains 12 to 14 percent $CO_2$, is an excellently suitable starting product. It may be used in powder or in paste form. Other carbonate containing aluminum hydroxide gel pastes which correspond to the USP XX standards are also quite suitable. The active aluminum hydroxides used in this process may be other commercially available aluminum hydroxide gels as well, particularly those produced from aluminum chloride.

Aluminum hydroxide gel powders according to USP XX may also be used. Examples of these are the commercially available products Alugel ® A 211 and Alugel ® A 215.

Combination products composed of USP XX defined active aluminum hydroxide gel and basic magnesium carbonate, which are commercially available as combined aluminum hydroxide magnesium carbonate dried gel, may also be used.

The water soluble, sulfate containing compounds used in this process may be aluminum sulfate, magnesium sulfate and sulfuric acid, as well as mixtures of these compounds. They are used in pharmaceutical purity in such quantities that the maximum amount of sulfate introduced is 17.5%, measured by reference to the resulting quantity of magaldrate. If magnesium sulfate alone is used, carbonate containing products result.

For the present process, active magnesium oxide is considered to be magnesium oxide in pharmaceutical purity which reacts with water to form magnesium hydroxide. The iodine number can be used to determine activity; it indicates how many mg iodine are bound by 1 g magnesium oxide. Magnesium oxides having an iodine number between 20 and 100 are particularly suitable as reactants.

Instead of magnesium oxide or a mixture of magnesium oxide with magnesium hydroxide, it is also possible to use magnesium hydroxide as the starting component. In the latter case, magnesium hydroxide in the form of suspensions (pastes) are preferably used. Magnesium hydroxide suspensions containing 30% $Mg(OH)_2$ are commercially available at various viscosities. A highly viscous magnesium hydroxide paste, for example, is Gilumag ® D 661 and a low viscosity paste is Gilumag ® D 611.

BRIEF DESCRIPTION OF THE DRAWINGS

FIG. 2 is the X-ray diffraction pattern for USP standard magaldrate. A comparison of FIGS. 1 and 2 indicates that the method of this invention results in the magaldrate of the same composition as the USP standard.

DESCRIPTION OF THE PREFERRED EMBODIMENTS

Figure 1:
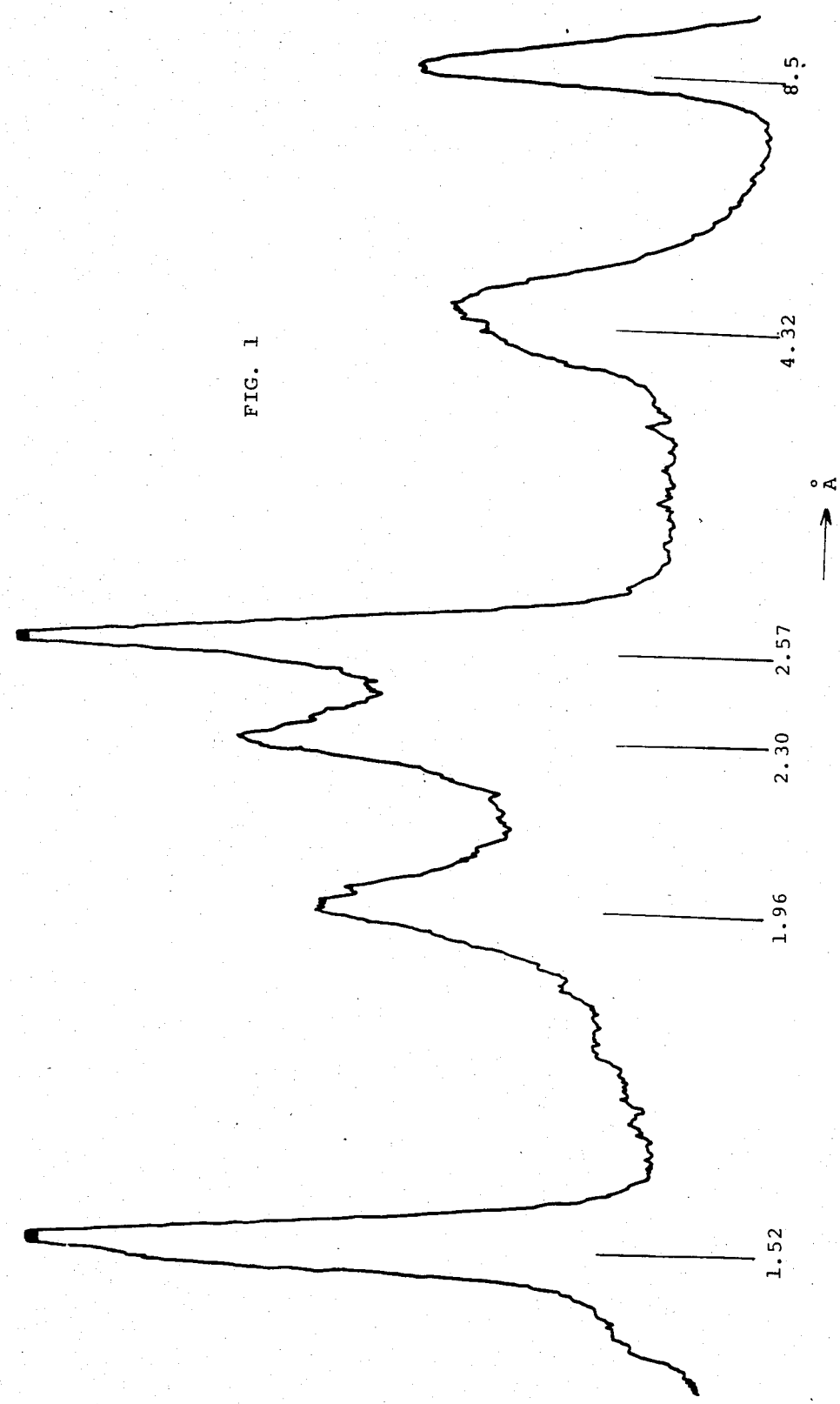
FIG. 1 is the X-ray diffraction pattern for magaldrate produced by the method of Example 1.

According to the preferred embodiment of the present invention, the process starts with active aluminum hydroxide in the form of a suspension or paste. Stoichiometric quantities of the sulfate containing compound, e.g. aluminum sulfate and/or sulfuric acid, dissolved in water are introduced while stirring. Upon termination of the carbon dioxide generation observed during this process, magnesium oxide, possibly diluted with water, is added while stirring further. The reaction sequence can be monitored by observing the increase in temperature. After standing for 10 to 24 hours, the paste is suitable for further processing, possibly after grinding in a colloid mill.

The resulting magaldrate is the basis for the calculation of the stoichiometric quantities.

The magaldrate paste produced according to the present invention can be used directly as the active ingredient in paste-like or liquid antacids. Alternatively, the magaldrate may be dried using known processes, e.g. by spray drying or roll drying.

It must be emphasized that, in the process of the present invention, not only is the selection of the starting materials critical—for example, no magaldrate is formed if industrial grade alumina (hydragillite) is used—but the sequence of the reaction steps is critical as well. A selection from among the stated reaction components and the order of their addition can be optimized without difficulty by conducting short preliminary experiments.

Generally, as already mentioned, the procedure will be such that the sulfate containing component is first added to the active aluminum hydroxide, after which the magnesium oxide is introduced. If, in this procedure, instead of magnesium oxide, magnesium hydroxide is used, no usable magaldrate is produced.

Magnesium hydroxide alone may be used, if the magnesium hydroxide is used as the starting substance. If magnesium hydroxide is first mixed with the sulfate containing component, and is thereafter mixed with the active aluminum hydroxide, usable, but carbonate containing, magaldrate is produced.

The subject matter of the present invention will now be explained in greater detail with the aid of the following examples.

EXAMPLE 1

In a glass beaker equipped with a propeller stirrer, 261 g aluminum hydroxide gel paste, USP XX, containing 10.26% $Al_2O_3$ (Alugel ® A 611) was used as the starting material. The paste was diluted with 250 ml water while stirring at room temperature. The diluted aluminum hydroxide gel paste was then mixed with 120 g aluminum sulfate solution having a density of 35° Bé, corresponding to an $Al_2O_3$ content of about 8% and a sulfate content of 22.6%. Stirring of the reaction mixture continued until the visually observable generation of $CO_2$ had substantially ceased, typically taking about 10 minutes. Then, while still stirring, 310 ml water was added and, thereafter, 58.4 g light magnesium oxide, USP XX, having the iodine number of 70, was introduced. During the incorporation of the magnesium oxide, the temperature rose noticeably. After addition of magnesium oxide, the stirrer was stopped and the mixture was left to stand for 24 hours. The reaction mixture could then be stirred easily and, to improve its consistency, it was passed through a laboratory colloid mill.

A carefully dried suspension sample was subjected to radiographic examination. For comparison purposes, a radiograph was made of a USP reference standard magaldrate. Evaluation and comparison of both radiographs indicated that magaldrate had formed in the novel process (see FIGS. 1 and 2). It was evident that the reaction was practically 100% from, inter alia, the determination of soluble sulfate in the suspension. The value of <1.9% sulfate (soluble) indicated that the major portion of the sulfate introduced was present in chemically bound form.

Further analytical examination of the suspension indicated a magnesium oxide content of 5.44%, an $Al_2O_3$ content of 3.64%, a sodium content of 0.007% and a pH of 9.1. The magaldrate content in the suspension could be calculated mathematically on the basis of the measured MgO and $Al_2O_3$ content, or on the basis of the quantity of sulfate added. Alternatively, the suspension could have been evaporated at 105° C. and the residue dried to a residual moisture content of not more than 10%. One method which has been very compatible with such a determination, and which was adhered to in the following procedures and has been found quite acceptable in practice was the determination of magaldrate content by measuring the acid neutralization capacity.

For this purpose, 10.0 g of the resulting magaldrate suspension was weighed and filled into a 250 ml glass beaker, and 30.0 ml of 1N hydrochloric acid was added while stirring until the solution was clear. Then 1N sodium hydroxide solution was used to retitrate the excess hydrochloric acid to a pH of 3. From the resulting acid consumption of 1N hydrochloric acid, the magaldrate content could be calculated, as 1 g magaldrate without water consumed 28.3 ml 1N hydrochloric acid.

The concentration in the suspension, in percent, of water-free magaldrate was equal to the spent 1N hydrochloric acid, expressed in ml, multiplied by the factor 100 and divided by 28.3. Accordingly, the magaldrate suspension produced according to this Example had a magaldrate content of 15.34%.

EXAMPLE 2

In a glass beaker equipped with a propeller stirrer, 50.6 g aluminum hydroxide gel powder, USP XX, Alugel®, type A 215, suspended in 500 ml $H_2O$, was used as the starting material. To this suspension, 120 g aluminum sulfate solution at a density of 35° Bé were added. After stirring for about 10 minutes, the mixture was diluted with 270 ml water. Then, 58.4 g light magnesium oxide, USP XX, having the iodine number 90, was stirred in.

After standing for 24 hours, the paste, which had settled in the meantime, could be stirred without difficulty. To improve sedimentation, stability and consistency, the suspension was passed through a laboratory colloid mill. The product was somewhat less viscous than the suspension produced according to Example 1, and had a greater tendency to settle.

Radiographic evaluation again indicated that magaldrate had formed, although the X-ray spectrum was less distinct than for the magaldrate of Example 1.

The magaldrate content of the suspension, determined by its acid neutralizing capacity, was 13.74% and the pH of the suspension was 9.8, determined in the same way as in Example 1.

EXAMPLE 3

In a glass beaker equipped with a stirring mechanism, 85.9 g spray dried aluminum hydroxide magnesium carbonate combined dried gel (type C 220) was suspended in 300 ml water. The $Al_2O_3$ content was about 42 weight percent and the MgO content was about 7 weight percent. While stirring, 28.1 g of concentrated sulfuric acid, diluted in 300 ml water, was added. After stirring for 10 minutes, 235 ml water was added, and then 51.9 g light magnesium oxide, USP XX, having the iodine number 30, was stirred in. The mixture was also left to stand for 24 hours. The sediment thus formed could be easily stirred. The resulting suspension was thin and had a slightly sandy character. To improve sedimentation, stability and consistency of the product, it was ground in a laboratory colloid mill.

Radiographic evaluation clearly indicated the formation of magaldrate. Concentration, determined by acid consumption, was 14.77% and the pH of the suspension was 8.0.

EXAMPLE 4

In a glass beaker equipped with a stirring mechanism, 357 g aluminum hydroxide gel paste, USP XX, Alugel®, type A 611, containing 10.2% $Al_2O_3$ was introduced as the starting material and was diluted with 150 ml water. Then 69.5 g magnesium sulfate heptahydrate, dissolved in 375 ml water, was added. While continuing to stir, 46.8 g light magnesium oxide, USP XX, having the iodine number 70, was worked in. The mixture was left to stand for 24 hours, and was then stirred and, in order to improve consistency of the product, was passed through a laboratory colloid mill.

Radiographic evaluation clearly indicated the formation of magaldrate; concentration, determined by way of acid consumption, was about 15.52%. The pH of the suspension was measured to be 7.8.

Further examination of the resulting product indicated a water soluble sulfate component of clearly more than 1.9%. It was further evident that the $CO_2$ content of the suspension was noticeably higher than that of the suspensions of other experimental products. The $CO_2$ content of 1.6% correspond to practically the entire quantity of $CO_2$ introduced with the aluminum hydroxide gel.

EXAMPLE 5

In a glass beaker equipped with a stirring mechanism, 357 g of a highly viscous aluminum hydroxide gel paste, USP XX, Alugel®, type A 661, containing 10.2% $Al_2O_3$ was diluted with 150 ml water. While stirring, 28.1 g concentrated sulfuric acid, diluted with 300 ml water, was added. After stirring for 10 minutes, 58.4 g light magnesium oxide, USP XX, having the iodine number 70, was added. The mixture was left to stand for 24 hours. The resulting reaction mixture could easily be stirred, but was, however, in order to improve its consistency, passed through a laboratory colloid mill. Radiographic evaluation clearly indicated the formation of magaldrate. The magaldrate concentration of the suspension, determined by way of its acid consumption, was 15.57% and its pH was 8.2.

EXAMPLE 6

In a 150 liter reaction vessel equipped with a stirring mechanism, 38.8 kg aluminum hydroxide gel paste, USP XX, Alugel®, type A 611, containing 10.2% $Al_2O_3$ was introduced as the starting mixture. This was initially further diluted while stirring with 35.6 liters of water. Then, while stirring, 16.8 kg of 35° Bé aluminum sulfate solution was added. Stirring continued until the visually observable gas generation was completed. Then 8.8 kg magnesium oxide, USP XX, having the iodine number 70, was added and was homogeneously dispersed in the mixture by further stirring. While the temperature rose to about 60° C., the viscosity of the paste clearly increased. While stirring, the paste was cooled to room temperature. The resulting 100 kg magaldrate paste had a magaldrate content of 23 weight percent. According to analytical and radiographic evaluation, magaldrate had been formed.

The consistency of the product obtained from this mixture was such that adjuvants could still be directly worked in, but it was dense enough to be stable against sedimentation.

This example demonstrated that magaldrate concentrations of up to 23 weight percent could be obtained using this novel process. It was even possible to obtain concentrations of 25 to 30%. However, at those concentrations the pastes had higher viscosities.

EXAMPLE 7

In a stainless steel reaction vessel, 3,278 kg aluminum hydroxide gel paste, USP XX, Alugel ® A 611, containing 11.37% $Al_2O_3$ was introduced as the starting mixture and diluted with 5,500 liter water while stirring at ambient temperature. While stirring continued, 1,566 kg aluminum sulfate solution at 35° Bé was permitted to flow in. Stirring continued until gas generation had substantially ceased, i.e. no further gas development was visually detectable at the surface of the suspension. Then 750 kg of medium heavy magnesium oxide, USP XX, having the iodine number of 20, was added. The temperature of the suspension rose to about 60° C. The suspension was left to cool while stirring, and the consistency of the resulting magaldrate suspension, containing 19% magaldrate, was such that it could be pumped directly into a spray dryer or another suitable drying apparatus.

Spray drying was carried out with an entrance temperature of 330° C. and an exit temperature of 115° C., and resulted in a yield of 2,100 kg magaldrate powder. The analytical results of the product of spray drying were:
Description
White, odorless, crystalline powder
Identification
(a) magnesium: positive
(b) aluminum: positive
(c) X-ray diffraction corresponding to that of the USP magaldrate reference standard in a range from 0.18 to 2.20 Nm.
Solubility
Insoluble in water and alcohol, soluble in diluted mineral acids
Magnesium (MgO): 31.18%
Aluminum ($Al_2O_3$): 21.03%
Moisture Content at 105° C., three hours: 3.97%
Chloride, water soluble (Cl): trace
Sodium (Na): 0.07%
Sulfate, water soluble ($SO_4$): <1.9%
Arsenic (As): <8 ppm
Heavy Metals (such as Pb): <60 ppm
E. coli: not detectable
The product met the standards of USP XX.

EXAMPLE 8

In a glass beaker equipped with a stirring mechanism, 67.6 g magnesium hydroxide paste, USP XX, Gilumag ® D 611, having an $Mg(OH)_2$ content of 30.5 weight percent was introduced as the starting mixture. Into this mixture, 28.25 g of an 8% aluminum sulfate solution was stirred. The result was a highly viscous paste which was diluted while stirring with 91.7 ml water. The resulting easily mixed suspension was mixed with 62.4 g of an aluminum hydroxide gel paste, USP XX (A 611), having an $Al_2O_3$ content of 10.2%. The result was a paste which, after standing for 24 hours, could be easily stirred. The resulting magaldrate had a somewhat sandy character and settled. The product could be homogenized by subsequent grinding.

The magaldrate concentration of the paste was 15.5 weight percent, and the soluble sulfate content in the dried product was 1.7%. The MgO content of the paste was 5.70%, the $Al_2O_3$ content was 3.60% and the bound $SO_4$ content was 2.55%.

A sample of the magaldrate produced by the method of Example 1 was finely ground and homogenised in an agate mortar. The homogenised magaldrate was fixed by pressing in a brass arrangement which had a diameter of 32 mm and a height of 0.8 mm. For the measurement an automatic Pulverdiffractometer, Type APD 15 (Philips Corp.) with a graphite monochromator was applied. The $K_{a1}$- and $K_{a2}$-lines were separated according Rachinger. For the measurement a scintillation counter was employed.

Operating voltage (Betriebsspannung): 45 kV
Current (Strom): 25 mA
Radiation (Strahlung): 10 CU $K_{a1}$(1,54050A)
Sensivity (Empfindlichkeit): $1 \times 10^3$ Impulse
dampening (Dämpfung): 4
scanning speed (Vorschubgeschwindigkeit): 4 cm/Min.

FIG. 1 shows the X-ray defraction pattern for the magaldrate product of Example 1, while FIG. 2 shows a similar pattern for USP standard magaldrate.

The evaluation of the diffraction pattern (FIG. 1) was carried out by comparing with the diffraction pattern for USP standard magaldrate (FIG. 2). The impulses are plotted on the ordinate and the d-spacings, in Angstrom units, on the abcissa.

Although this invention is shown by the embodiments described in the examples above, it is to be understood that the invention is not to be limited by these examples but extends to all embodiments within the scope of the following claims and their equivalents.

What is claimed is:

1. A process for producing magaldrate of the formula,

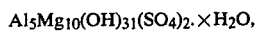

comprising mixing an aqueous suspension of carbonate containing active aluminum hydroxide with an aluminum sulfate solution in stoichiometric quantities under intensive stirring; after the generation of carbon dioxide ceases, mixing in stoichiometric quantities of magnesium oxide having an iodine number between 20 and 100; and allowing the resulting mixture to stand for 10 to 24 hours without mixing to form magaldrate paste.

2. The process of claim 1, wherein the magaldrate paste is dried directly, without filtration, washing or rehomogenization.

3. The process of claim 1, wherein the magaldrate paste is further processed to form magaldrate powder.

4. A process for producing magaldrate of the formula,

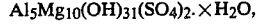

comprising combining magnesium hydroxide with at least one water soluble sulfate containing compound in the presence of water and in stoichiometric quantities while stirring, thereafter adding stoichiometric quantities of active aluminum hydroxide while continuing to stir, and allowing the resulting mixture to stand without mixing to form magaldrate paste.

5. The process of claim 4, wherein the magaldrate paste is dried directly, without filtration, washing or rehomogenization.

* * * * *